(12) United States Patent
Ramnarine

(10) Patent No.: US 7,537,451 B1
(45) Date of Patent: May 26, 2009

(54) DENTAL HYGIENE APPARATUS

(76) Inventor: Amrish Ramnarine, 983 Windward Way, Weston, FL (US) 33327

( * ) Notice: Subject to any disclaimer, the term of this patent is extended or adjusted under 35 U.S.C. 154(b) by 0 days.

(21) Appl. No.: 11/946,949

(22) Filed: Nov. 29, 2007

Related U.S. Application Data

(60) Provisional application No. 60/861,677, filed on Nov. 29, 2006.

(51) Int. Cl.
*A61C 15/00* (2006.01)
*A61C 9/00* (2006.01)
*A61H 7/00* (2006.01)

(52) U.S. Cl. .................... 433/216; 433/37; 601/164; 15/22.1

(58) Field of Classification Search ............ 433/37, 433/80, 216; 15/167.1, 167.2, 22.1; 128/861, 128/862; 601/162–165
See application file for complete search history.

(56) References Cited

U.S. PATENT DOCUMENTS 3,440,680 A * 4/1969 Werding ............... 15/321
4,223,417 A * 9/1980 Solow ................. 15/22.1
4,795,347 A * 1/1989 Maurer ................ 433/216

\* cited by examiner

*Primary Examiner*—Cris L Rodriguez
*Assistant Examiner*—Matthew M Nelson
(74) *Attorney, Agent, or Firm*—Gold & Rizvi, P.A.; H. John Rizvi; Glenn E. Gold

(57) ABSTRACT

A dental hygiene apparatus including a mouthpiece formed of a flexible arcuate channel defining and inner space designed for receiving an upper or lower set of human teeth. The channel is provided with longitudinally extending tunnels interconnected by communicating passageways. Each of the tunnels is provided with a longitudinally extending track and a guide slot communicating with the inner space. A carriage assembly includes motor assemblies joined by rigid chassis rods. The carriage assembly is designed such that the motor assemblies may be disposed in the tunnels while the chassis rods are disposed in the passageways. The motor assemblies have a shaft extending through one of the guide slots and carrying a rotatably mounted cleaning head on a distal end. The motor assemblies also include a driven wheel resting on a one of the tracks, for propelling the carriage assembly along the tracks. The cleaning heads rotate to clean the teeth and travel along the tracks to clean each tooth in sequence.

4 Claims, 4 Drawing Sheets

DENTAL HYGIENE APPARATUS

CROSS-REFERENCE TO RELATED APPLICATION

This application claims the benefit of co-pending U.S. Provisional Patent Application Ser. No. 60/861,677, filed Nov. 29, 2006, which is incorporated herein in its entirety.

BACKGROUND OF THE INVENTION

1. Field of the Invention

The present invention relates generally to a dental hygiene apparatus consisting of a mouthpiece with motor driven cleaning heads traveling on tracks within the mouthpiece. The mouthpiece is designed to fit onto a user's teeth and the cleaning heads are configured to rotate and to travel along the tracks to clean dental surfaces. The apparatus sequentially cleans and polishes each tooth and adjacent gums to remove plaque and residue, thus eliminating the need for standing in front of a bathroom mirror to brush, and providing a portable hands-free dental hygiene apparatus to promote regular and frequent dental maintenance.

2. Description of the Prior Art

Oral disease has plagued human beings since the beginning of history, but it was not until dentistry advanced to the stage of detecting bacteria responsible for periodontal disease, that preventive dentistry became important. Public concern regarding the risks of contracting infectious diseases through dental procedures, has heightened awareness of the importance of dental hygiene and has increased the desire for more sophisticated dental equipment to better maintain teeth, for health, as well as aesthetic reasons.

Tooth brushing is the mainstay of basic dental hygiene. Existing tooth brushing techniques, however, are not without their disadvantages. To begin with, the use of a toothbrush requires the user have access to a sink. Many times throughout the day, people consume snacks and meals, and use of a sink to maintain dental hygiene is not very practical. As a result, proper cleansing of the mouth and gums does not occur after every meal, making teeth more susceptible to plaque, decay, and periodontal disease, such as gingivitis.

Furthermore, many people do not know or utilize proper brushing techniques when cleaning their teeth with a toothbrush. Up and down movements are simply not enough when trying to maintain the proper level of care to prevent tooth and gum disease. Specific amounts of pressure, rotation, and time must be applied to each tooth for proper dental hygiene and maintenance.

Accordingly, there is an established need for a dental hygiene apparatus that, in addition to eliminating the necessity of access to a sink during teeth cleaning, also provides a portable, hands-free means for proper dental maintenance, and promotes frequent and regular dental care by the user, allowing them to partake in other activities while simultaneously engaging in the dental hygiene process.

SUMMARY OF THE INVENTION

The present invention is directed to a dental hygiene apparatus comprising a portable device, configured for fitting onto a user's teeth and operable to clean each tooth and adjacent gum. The device can be worn during a wide variety of activities and eliminates the need for access to a sink to brush teeth. Consistent and proper dental hygiene can be practiced conveniently and in a hands-free manner.

An object of the present invention is to provide a dental hygiene apparatus that utilizes a multi-brush system.

A further object of the present invention is to provide a dental hygiene device that provides rotational brushing techniques in a hands-free method.

Another object of the present invention is to provide a dental hygiene apparatus that brushes the teeth, while simultaneously polishing away plaque and residue to reduce or eliminate tooth and gum disease.

The dental hygiene apparatus comprises a mouthpiece, multiple traveling cleaning heads and actuating means for the cleaning heads. The mouthpiece includes an arcuate channel formed of flexible material having a base portion and two opposed, spaced apart, wall portions, a first wall portion and a second wall portion, both projecting from the base portion. The base portion and the wall portions define an inner space sized to receive an upper or lower set of human teeth. The mouthpiece includes a first longitudinally extending side track mounted in a first tunnel on an inner aspect of the first wall portion and a second longitudinally extending side track mounted in a second tunnel on an inner aspect of the second wall portion. The mouthpiece includes a longitudinally extending base track mounted in a third tunnel on an inner aspect of the base. A carriage assembly includes actuating means and is configured to travel along the tracks, through the tunnels. The actuating means includes a plurality of motor assemblies to propel the carriage assembly along the tracks and to rotate the cleaning heads. The mouthpiece may be placed onto an upper or lower set of teeth and the actuating means may be energized to rotate the cleaning heads and to traverse the carriage assembly along the tracks to sequentially clean the top and side surfaces of teeth together with adjacent gums. Each of the cleaning heads may be provided with a face having outwardly extending bristles, flexible fingers, and a cleaning sponge to promote removal of deposits on the teeth.

The motor assemblies include electric motors and one or more electrical switches for rotating and traversing the cleaning heads.

Power, for the electric motors is provided by batteries carried in the motor assemblies and connected to the electric motors and to the switches by wiring according to conventional practice.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION OF THE PREFERRED EMBODIMENTS

Shown throughout the figures, the present invention is generally directed towards a dental hygiene apparatus, designed specifically to provide users with a practical and efficient means for practicing dental hygiene in a compact, flexible structure that eliminates the need to use a sink or hands, while providing proper dental maintenance, promoting frequent and regular dental cleaning, and allowing the user to partake in an array of activities during this process.

Figure 1:
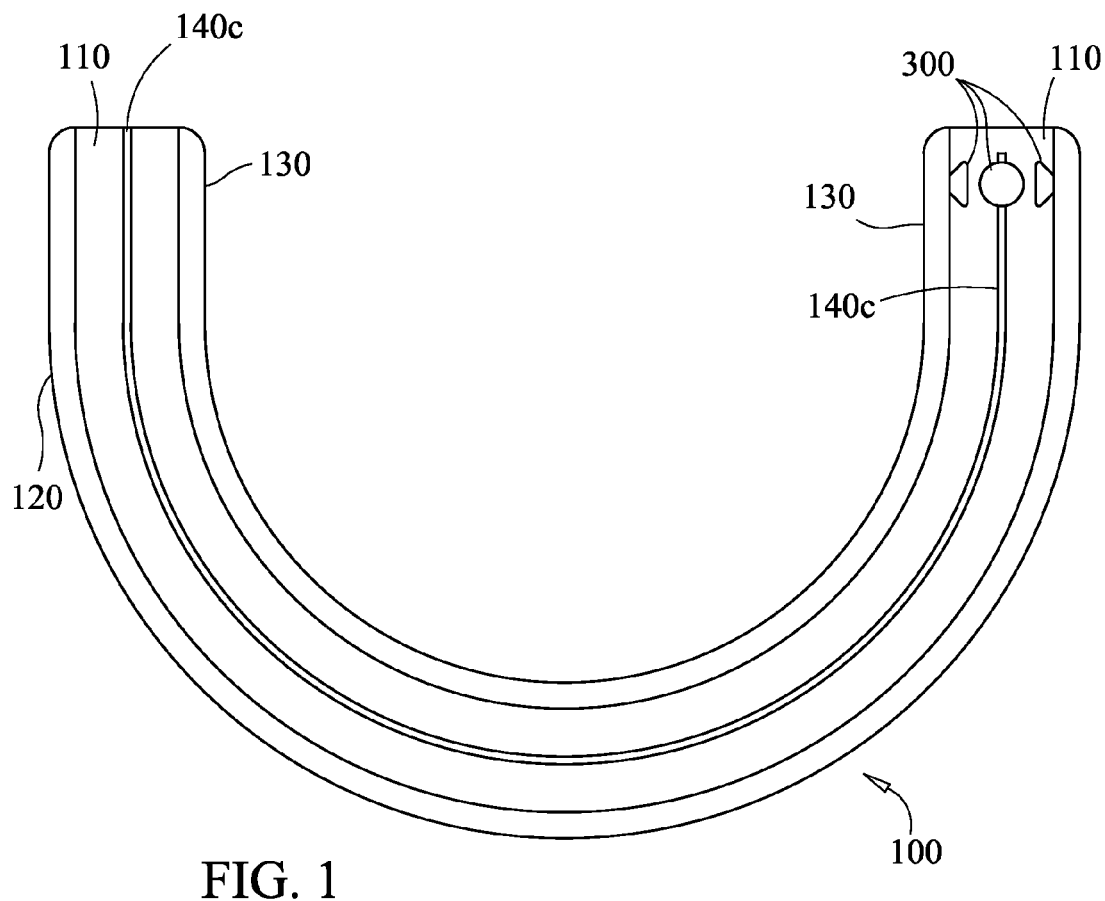
FIG. 1 is a plan view of the dental hygiene apparatus, showing the inner space of the channel, the cleaning heads, and the third guide slot.
Figure 2:
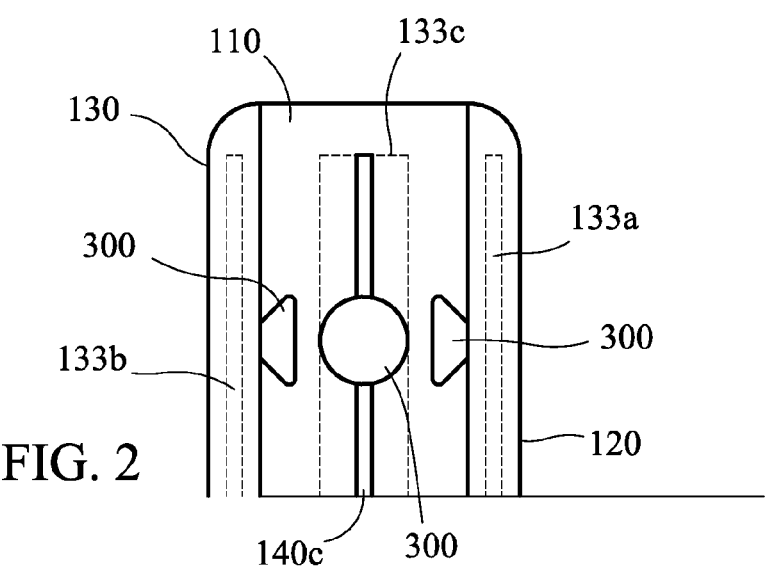
FIG. 2 is a close-up plan view showing an end portion of the channel with the cleaning heads and the tunnels shown in phantom lines.

Referring now to FIGS. 1 and 2, the dental hygiene apparatus 100 is composed of an arcuate channel including a base portion 110, a first wall portion 120 and a second wall portion 130. Each of the first and second wall portions 120 and 130 project from the base portion 110 in spaced apart relation which, with the base portion 110, define an inner space configured for receiving an upper or lower set of teeth of an individual, as shown in FIG. 1. The channel is preferably molded of flexible material such as plastic, rubber, and combinations thereof, or any of a wide variety of other known materials without departing from the present invention. Material used for forming an athletic mouth guard is suitable for forming the channel.

Figure 3:
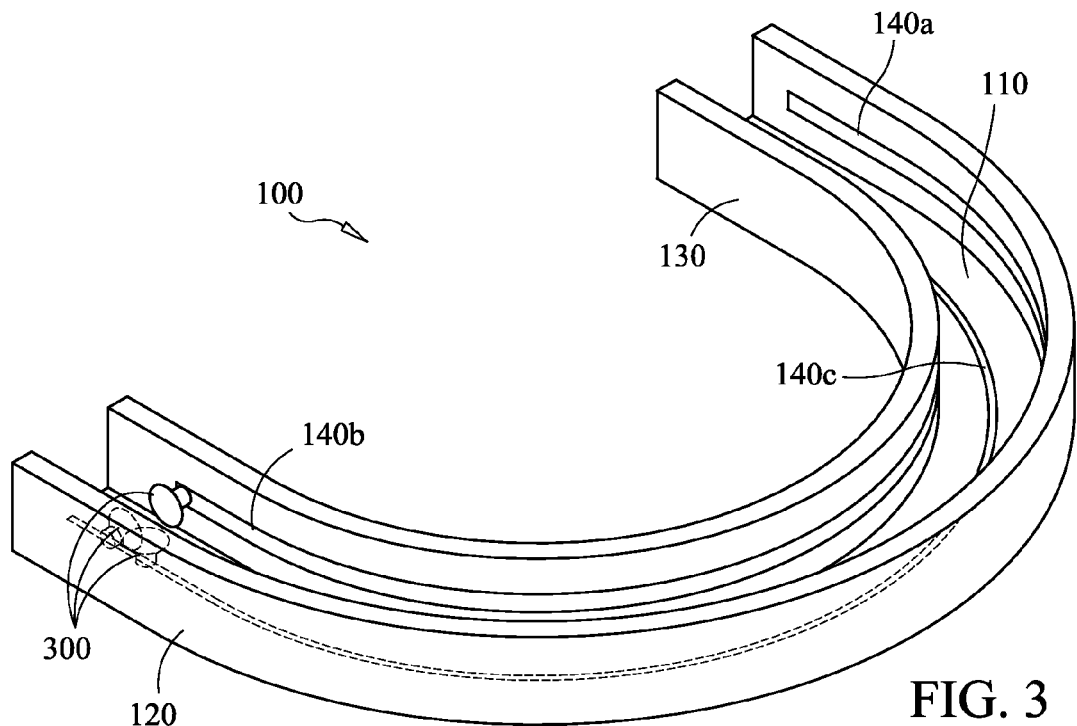
FIG. 3 is a perspective view of the dental hygiene apparatus with the base track shown partially in phantom mode and with the apparatus oriented for placement on an upper set of teeth.
Figure 5:
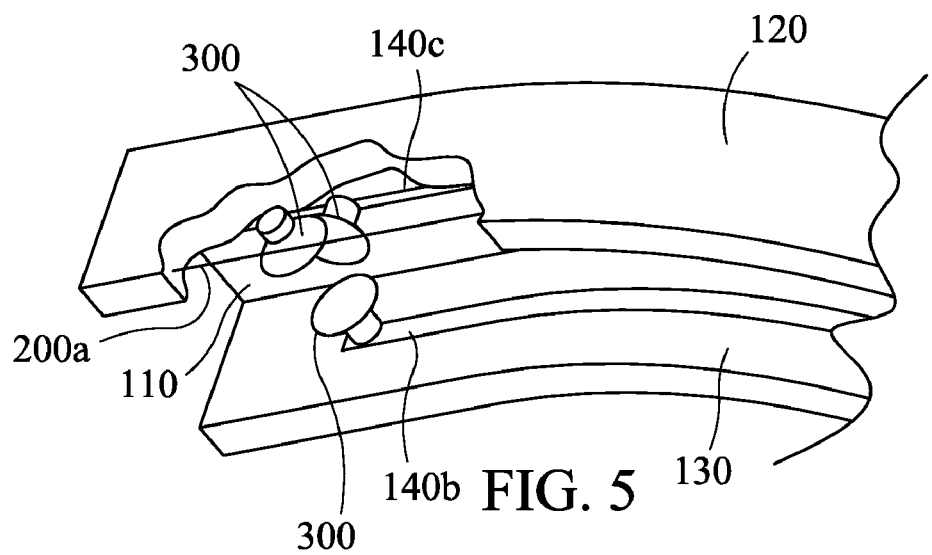
FIG. 5 is a cut-away view of a portion of the dental hygiene apparatus showing two of the cleaning heads and a portion of the first track.

As shown in FIG. 2, a first tunnel 133a is provided in the first wall portion 120. The first tunnel 133a is located proximate to an inner aspect of the first wall portion 120 and extends longitudinally along an intermediate portion of the channel. As shown in FIG. 3, a first guide slot 140a communicates between the first tunnel 133a and the inner space being coextensive with the first tunnel 133a. A first longitudinally extending side track 200a is mounted in the first tunnel 133a of the first wall portion 120. The first side track 200a, as shown in FIG. 5, is likewise coextensive with the first tunnel 133a. A second tunnel 133b is provided in the second wall portion 130. The second tunnel 133b is located proximate to an inner aspect of the second wall portion 130 and extends longitudinally along an intermediate portion of the channel. A second guide slot 140b communicates between the second tunnel 133b and the inner space being coextensive with the second tunnel 133b. A second longitudinally extending side track 200b is mounted in the second tunnel 133b of the second wall portion 130. The second side track 200b is likewise coextensive with the second tunnel 133b. A third tunnel 133c is located proximate to an inner aspect of the base portion 110 and extends longitudinally along an intermediate portion of the channel. A third guide slot 140c communicates between the third tunnel 133c and the inner space being coextensive with the third tunnel 133c. A longitudinally extending base track 200c is mounted in the third tunnel 133c of the base portion 110. The base track 200c is likewise coextensive with the third tunnel 133c. The tracks 200a, 200b, and 200c are preferably formed of stainless steel wire of the type used for tensioning orthodontic appliances. The tracks 200a, 200b, and 200c may preferably be attached by a plurality of brackets 210 attached to the tracks 200a, 200b, and 200c by soldering and being embedded in the channel. A first passageway 142a communicates between the third tunnel 133c and the first tunnel 133a and a second passageway 142b communicates between the third tunnel 133c and the second tunnel 133b. The passageways 142a and 142b are coextensive with the tunnels 133a, 133b, and 133c.

Figure 7:
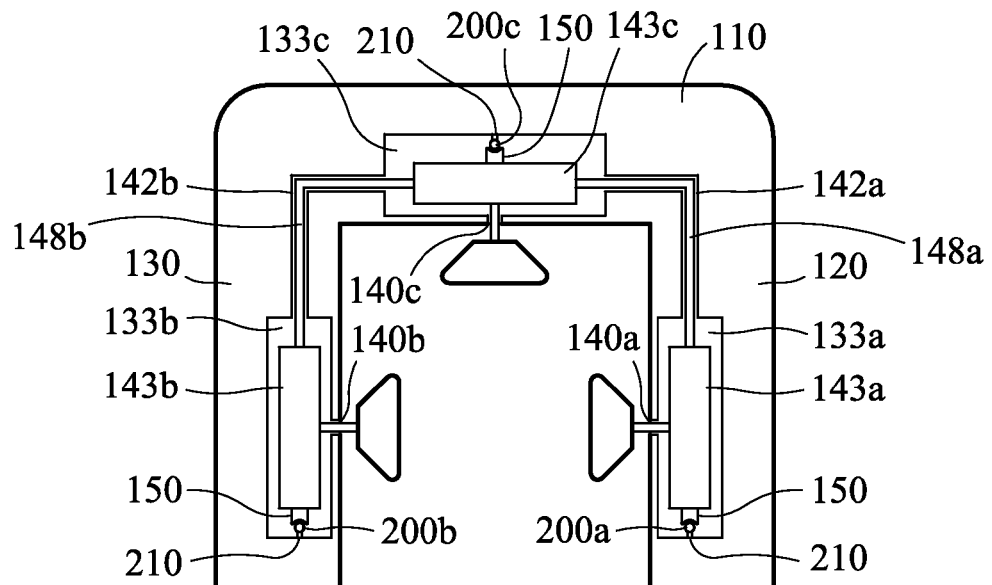
FIG. 7 is a cross-sectional view of portion of the dental hygiene apparatus showing the tunnels and carriage assembly.

Actuating means may include three motor assemblies contained in housings. As shown in FIG. 7, a first motor assembly 143a is disposed inside the first tunnel 133a. A second motor assembly 143b is disposed inside the second tunnel 133b. A third motor assembly 143c is disposed inside the third tunnel 133c. Each of the three motor assemblies includes a motor with two output means. A first high speed output means is a rotating shaft extending outward through a guide slot into the inner space and a cleaning head 300 is mounted on a distal end. A second lower speed output means is a rotating wheel 150 configured with a concave rim and resting on a one of the tracks. Each motor assembly includes a motor, a battery for providing power and conventional switch and wiring for connecting the battery to the motor.

Figure 8:
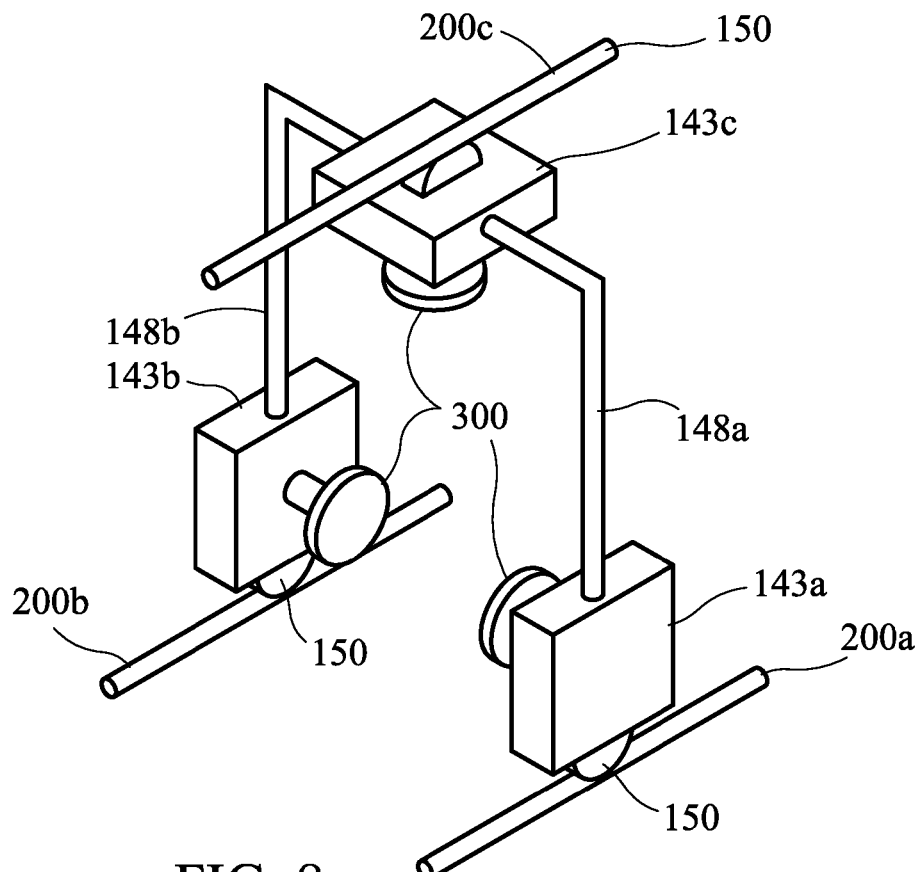
FIG. 8 is a perspective view of the carriage assembly of the present invention.

The motor assemblies 143a, 143b, and 143c are rigidly connected by chassis rods to form a unitary carriage assembly 145, as shown in FIG. 8. A first chassis rod 148a connects the first motor assembly 143a to the third motor assembly 143c and lies in the first passageway 142a. A second chassis rod 148b connects the second motor assembly 143b to the third motor assembly 143c and lies in the second passageway 142b. It is intended that the motors rotate the cleaning heads and also drive the wheels 150 to cause the carriage assembly to traverse the tracks with the motor assemblies traveling through the tunnels and the chassis rods traveling through the passageways. For stability, each of the motor assemblies may be designed with more than one wheel 150. Other conventional means of propelling the carriage assembly 145 along the tracks may be employed.

Figure 4:
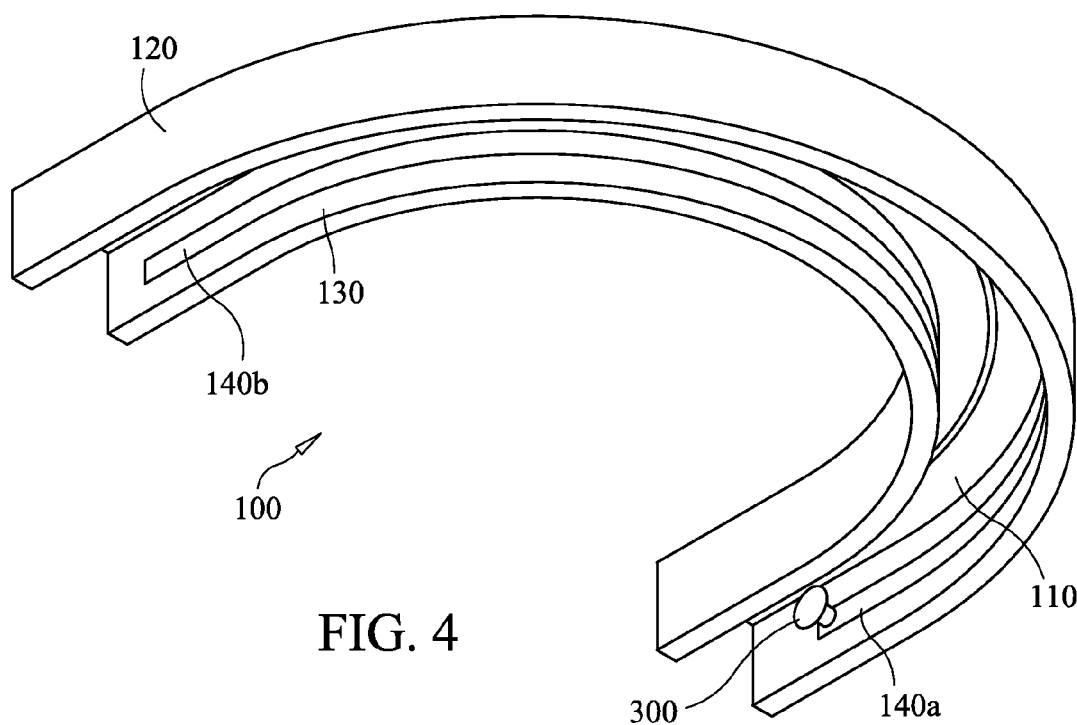
FIG. 4 is a perspective view of the dental hygiene apparatus with the apparatus oriented for placement on a lower set of teeth.

Referring now to FIGS. 3 and 4, the apparatus is depicted in suitable orientation for placement on upper teeth in FIG. 3 and in suitable orientation for placement on lower teeth in FIG. 4. It is intended that a user may place the apparatus on the upper set of teeth, as a first step, and subsequently place the apparatus on the lower set of teeth as a second step. It will also be appreciated by those skilled in the art that two apparatus of the present invention may be used simultaneously to clean upper and lower teeth in one step.

Referring now to FIG. 5, a cut-away view of a portion of the dental hygiene apparatus 100 reveals part of the second guide slot 140b, in which the high speed output shaft of the second motor assembly 143b slides along the channel while rotating one of the cleaning heads 300. The first wall portion 120 is partially cut away to reveal the first track 200a which extends through the first tunnel 133a and provides traction for the wheel 150 of the first motor assembly 143a. The other cleaning heads 300 traverse the channel to clean the top and sides of a set of teeth in much the same manner.

Figure 6:
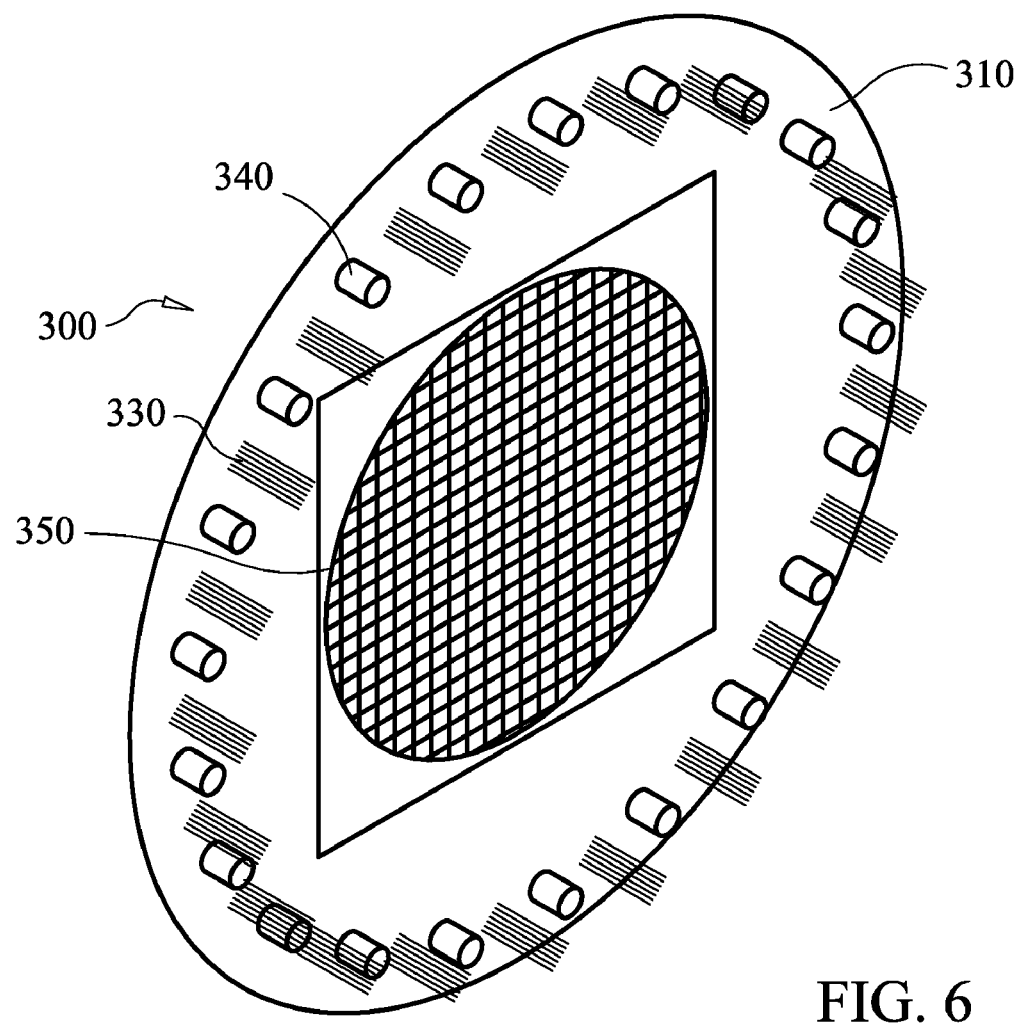
FIG. 6 is a perspective view of a cleaning head depicting the bristles, fingers, and sponge.

The cleaning heads 300 are preferably formed of rubber and have a rounded face 310, as shown in FIG. 6. The face 310 includes bristles 330, which may be composed of fibers having differing degree of stiffness. It will be apparent to those skilled in the art that bristles located proximate to the periphery of the face 310 will move more rapidly than bristles located proximate to the center of the face 310. The stiffness and location of particular bristles may be selected to obtain various cleaning action, as desired. Also, the bristles 330 located on the face 310 of the cleaning heads 300 shall be made of soft fibrous material. Rubber fingers 340 are also provided on the face 310 and project outward to remove debris from teeth. It is preferred that the face 310 also include a sponge 350 for additional cleaning capability. It will be appreciated that the cleaning heads 300 may be modified to incorporate means for delivery of ultra-sound or light energy to augment the cleaning capability of the apparatus.

The length of the bristles 330, the cleaning heads connected to the first motor assembly 143a and on the second motor assembly 143b is to be selected so that contact is made in the area where the gum and teeth connect, removing plaque build-up. The length of the bristles 330 on the cleaning head connected to the third motor assembly 143c is to be selected such that enamel is preserved on the tooth, and only foreign matter is removed.

Since many modifications, variations, and changes in detail can be made to the described preferred embodiments of the invention, it is intended that all matters in the foregoing description and shown in the accompanying drawings be interpreted as illustrative and not in a limiting sense.

What is claimed is:

1. A tooth and gum cleaning apparatus comprising:
   a mouthpiece, multiple traveling cleaning heads, and actuating means for said cleaning heads;
   said mouthpiece including an arcuate channel formed of flexible material;
   said channel having a base portion, a first wall portion, and a second wall portion;
   said first wall portion and said second wall portion project from said base portion defining an inner space sized for receiving an upper or lower set of human teeth;
   said mouthpiece including a first longitudinally extending side track mounted in a first tunnel provided in said first wall portion, a second longitudinally extending side track mounted in a second tunnel provided in said second wall portion, and a longitudinally extending base track mounted in a third tunnel provided in said base portion;
   each of said tracks having at least one of said cleaning heads traveling thereon;
   each of said tunnels having a longitudinally extending guide slot communicating with said inner space;
   said actuating means being disposed in said tunnels and said cleaning heads being disposed in said inner space adjacent to said teeth;
   said actuating means being operably connected to said cleaning heads through said guide slots and being configured to rotate said cleaning heads and to propel said cleaning heads along said tracks;
   whereby said mouthpiece may be placed onto an upper or lower set of teeth and said actuating means may be energized to rotate and to traverse said cleaning heads for sequentially cleaning top and side surfaces of teeth and adjacent gums.

2. The tooth and gum cleaning apparatus of claim 1, wherein:
   a first longitudinally extending passageway is provided in said channel;
   said first passageway being shaped to communicate between said first tunnel and said third tunnel;
   a second longitudinally extending passageway is provided in said channel;
   said second passageway being shaped to communicate between said second tunnel and said third tunnel;
   said actuating means comprises a carriage assembly having a first motor assembly, disposed in said first tunnel, a second motor assembly, disposed in said second tunnel, and a third motor assembly, disposed in said third tunnel;
   said first motor assembly being joined to said third motor assembly by a rigid first chassis rod disposed in said first passageway;
   said second motor assembly being joined to said third motor assembly by a rigid second chassis rod disposed in said second passageway;
   each of said motor assemblies having means for rotating a one of said cleaning heads and means for propelling said carriage assembly along said tracks.

3. The dental hygiene apparatus of claim 2 wherein:
   each of said motor assemblies includes a motor, a rotating shaft, a driven rotatably mounted wheel, and a power supply;
   said motor being operably connected to said output shaft;
   said shaft extending through a one of said guide slots;
   a one of said cleaning heads being mounted on a distal end of said shaft;
   said wheel resting in contact with a one of said tracks;
   said power supply being operably connected for energizing said motor;
   whereby said motor assemblies may be energized for rotating said cleaning heads and for propelling said carriage assemblies along said tracks.

4. The dental hygiene apparatus of claim 1, wherein, said cleaning heads include bristles, flexible fingers, and a sponge, for cleaning said teeth.

\* \* \* \* \*